(12) United States Patent
Griego et al.

(10) Patent No.: US 7,118,584 B2
(45) Date of Patent: *Oct. 10, 2006

(54) STEERABLE SPHINCTEROTOME AND METHODS FOR CANNULATION, PAPILLOTOMY AND SPHINCTEROTOMY

(75) Inventors: John A. Griego, Blackstone, MA (US); Yem Chin, Burlington, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/436,074

(22) Filed: May 13, 2003

(65) Prior Publication Data

US 2003/0191486 A1   Oct. 9, 2003

Related U.S. Application Data

(63) Continuation of application No. 09/761,843, filed on Jan. 18, 2001, now Pat. No. 6,579,300.

(51) Int. Cl.
*A61B 17/32* (2006.01)

(52) U.S. Cl. ............ 606/167; 606/41; 606/171; 606/159; 606/113; 604/164.08

(58) Field of Classification Search ........... 606/167, 606/41, 171, 113, 159, 170, 172, 174; 604/164.08, 604/22, 540, 43, 28; 600/463
See application file for complete search history.

(56) References Cited

U.S. PATENT DOCUMENTS

| | | | | |
|---|---|---|---|---|
| 5,181,920 A | * | 1/1993 | Mueller et al. | 606/159 |
| 5,487,757 A | | 1/1996 | Truckai et al. | |
| 5,599,299 A | * | 2/1997 | Weaver et al. | 604/540 |
| 5,643,199 A | * | 7/1997 | Rowland et al. | 604/22 |
| 5,827,313 A | * | 10/1998 | Ream | 606/171 |
| 5,947,925 A | * | 9/1999 | Ashiya et al. | 604/164.08 |
| 6,423,059 B1 | * | 7/2002 | Hanson et al. | 606/41 |
| 6,579,300 B1 | * | 6/2003 | Griego et al. | 606/167 |
| 6,602,262 B1 | * | 8/2003 | Griego et al. | 606/113 |

* cited by examiner

*Primary Examiner*—Robin O. Evans
*Assistant Examiner*—Leonid M. Fastovsky
(74) *Attorney, Agent, or Firm*—Fulbright & Jaworski LLP

(57) ABSTRACT

The present invention relates to methodology of and apparatus for accurately positioning devices for performing endoscopic cannulation, papillotomy and sphincterotomy and similar procedures. The sphincterotome with a steerable or adjustable distal segment of the present invention allows the physician to control the position of the distal tip of the device independently of the endoscope and adjust for inconsistencies in the device and the anatomy. According to one embodiment of the present invention, a threaded portion of a cable assembly cooperates with a torque transmission element and a cog to enable the operator to rotate a cutting wire into a desired position relative to the catheter. Alternate embodiments allow the operator to fix the depth of a needle knife while allowing, if desired, accurate rotational positioning of the associated catheter. Threaded stabilizing elements, pivot elements and a steering wire may be used together or individually to accomplish these features. Presently available products that may be modified according to the present invention include, but are not limited to, Boston Scientific Sphincterotomes and Needle Knives.

10 Claims, 9 Drawing Sheets

STEERABLE SPHINCTEROTOME AND METHODS FOR CANNULATION, PAPILLOTOMY AND SPHINCTEROTOMY

This is a continuation of U.S. Ser. No. 09/761,843 filed Jan. 18, 2001, now U.S. Pat. No. 6,579,300.

The present invention is an improvement of the devices and methods disclosed in U.S. Pat. No. 5,547,469, U.S. Pat. No. 5,868,698 and U.S. Pat. No. 5,683,362 and in U.S. patent application Ser. No. 09/154,834 in the name of Rowland, et al., all owned by the owner of the present application, and incorporated in their entirety.

BACKGROUND

1. Field of the Invention

This invention generally relates to apparatus that is useful in performing diagnostic and therapeutic modalities in the biliary tree and more particularly to apparatus that is adapted for facilitating the diagnosis of gallstones in the bile duct and other portions of the biliary tree and the removal of such gallstones.

2. Description of Related Art

According to the present state of the art, endoscopic cannulation of the common bile duct and papillotomy and/or sphincterotomy of the Papilla of Vater and/or the Sphincter of Oddi is accomplished by advancing a sphincterotome (or papillotome or cannulotome) into an endoscope/duodenoscope so that the distal tip of the sphincterotome exits the endoscope adjacent the sphincter muscles at the Papilla of Vater. The endoscope mechanisms are then manipulated to orient the distal tip of the sphincterotome to the desired position for proper cannulation of the duct. Due to inconsistencies in the sphincterotome, anatomy, and endoscope manipulation, it is difficult to accurately and consistently position the sphincterotome for proper cannulation.

Historically the migration of gallstones into an individual's common bile duct was corrected by general surgical procedures. A surgeon would incise the bile duct and remove the gallstones and normally remove the gallbladder. In recent years less invasive treatment modalities have replaced these general surgical procedures and reduced patient trauma, long hospital stays and recovery periods.

For example, U.S. Pat. No. 4,696,668 and U.S. Pat. No. 4,781,677, both to Wilcox, disclose a treatment modality involving the administration of a dissolution agent in the bile duct to essentially dissolve any gallstones. More specifically, a catheter contains several lumens for inflating and deflating each of two balloons, venting bile, and infusing and aspirating the dissolution agent. Inflating the balloons occludes the bile duct at two spaced sites and creates a sealed spaced that receives the dissolution agent. As the space is sealed from the remaining biliary tree, the dissolution agent finds access to the gallbladder and any gallstones therein through the cystic duct with the exclusion of bile from the gallbladder fundus. The dissolution agent also will be confined in high concentration around bile duct gallstones. After the gallstones dissolve the balloons are deflated and the catheter can be withdrawn. In this particular approach, the catheter is directed into the biliary tree using a standard duodenoscope that passes through the alimentary tract. Although this and analogous approaches have the potential of minimizing patient trauma, such treatments require extended placement of the duodenoscope in the patient, exhibit low efficacy and introduce a potential for adverse reactions to the dissolution agents.

In an alternative approach, a surgeon directs a surgical extractor into the biliary tree through at least an incision in the bile duct. For example, in U.S. Pat. No. 3,108,593 to Glassman a surgeon incises both the bile duct and duodenum. Then the surgeon directs an extractor through the bile duct incision, biliary tree, sphincter of Oddi and duodenum to exit through the duodenum incision. This extractor includes a series of longitudinally spaced cages for trapping any gallstones in the bile duct and removing them through either of the incisions.

U.S. Pat. No. 4,627,837 to Gonzalo discloses a catheter device with a pair of inflatable balloons at its distal end. This catheter is led through an incision in the bile duct toward the duodenum. After the distal balloon passes through the sphincter of Oddi, both balloons are expanded to anchor the catheter in place. This enables the catheter to be used for irrigating and flushing through other lumens in order to capture any gallstone in the second balloon for removal through the incised bile duct.

In accordance with still another modality as for the treatment of strictures, a surgeon may insert a catheter device through the bile duct or duodenum for the purpose of dilating or enlarging the sphincter of Oddi. For example, U.S. Pat. No. 4,705,041 to Kim discloses a dilator that is directed through an incision in the bile duct and the sphincter of Oddi. An expandable tip dilates the sphincter of Oddi. U.S. Pat. No. 5,035,696 to Rydell discloses an electrosurgical instrument that is directed through the duodenum and to the sphincter of Oddi for performing a sphincterotomy. This apparatus contains a cutting wire that is heated to cut the sphincter muscle. U.S. Pat. No. 5,024,617 to Karpiel, discloses a similar device that can be directed through a duodenoscope. U.S. Pat. No. 5,152,772 to Sewell, Jr. discloses a device for performing a sphincterotomy that is directed through an incision in the bile duct and includes a knife for cutting the sphincter muscle.

The use of the duodenoscope and sphincterotomy devices, such as shown in the Rydell and Karpiel patents, enables an internist to diagnose and treat problems in the biliary tree with minimal patient invasion. For example, modalities as described in these patents eliminates the surgery needed for incising the bile duct. Consequently, these modalities can be performed as outpatient or day surgical procedures. These procedures greatly reduce patient trauma, the length of a hospital stay and recovery times. For example, if an internist determines that gallstones are present in the biliary tree, particularly the common bile duct, the internist can insert a duodenoscope into the duodenum to view the sphincter of Oddi. Then a first catheter can be advanced through the working channel of the duodenoscope with or without a guidewire and directed through the sphincter of Oddi into the biliary tree. Contrast agent injected through the catheter enables fluoroscopy or other imaging procedures to confirm the presence of gallstones within the biliary tree. Next the internist exchanges the first catheter for a second catheter for performing a sphincterotomy such as the types disclosed in the above-identified Rydell and Karpiel patents. The second catheter is then exchanged for a third catheter such as shown in the Glassman patent or some other equivalent retrieval catheter for drawings gallstones through the enlarged sphincter of Oddi. Thereafter the retrieval catheter is manipulated to release the gallstone into the duodenum. The catheter, any guidewire and the duodenoscope can then be removed to complete the procedure.

This procedure is significantly less traumatic to the patient than other prior art procedures because the only incision occurs during the sphincterotomy. However, this procedure, as described above, requires three separate catheters and two catheter exchanges. These exchanges are required because the first, second and third catheters function solely to inject contrast agent to perform the sphincterotomy and to dislodge gallstones, respectively. The time required for performing each catheter exchange can increase patient trauma and increase the duration of the procedure and reduce efficiency. Moreover, each such procedure requires the use of two or three separate catheter devices.

Multi-lumen catheters are available which typically reduce the number of catheters and catheter exchanges used during a procedure and thereby reduce both the time required and the patient's trauma while increase efficiency. The use of multi-lumen devices also eliminates the need for the repositioning of subsequent catheters because the original catheter was withdrawn. While the multi-lumen device may have to be repositioned, the repositioning is considerable less then when a single lumen catheter is used. While precision positioning of the multi-lumen device is essential for safe and effective results, accurate positioning of the multi-lumen device is difficult to achieve. State of the art multi-lumen devices are typically positioned by torque transmission from the handle to the distal tip approximately 6 feet away. Additionally, when an incision is made, proper knife depth is difficult to maintain because of the connection between the knife lumen and the knife shaft. When pressure is applied to the knife lumen an undesirable movement of the needle knife tip may occur because of this imprecise connection.

A need exists for an apparatus and a methodology of accurate placement of catheters, multi-lumen devices and needle knives. A further need exists for an apparatus for and a methodology of an accurate depth control for needle knives and other cutting instruments.

SUMMARY

Therefore, this invention provides an apparatus for, and a methodology of, accurate placement of the catheter, papillotome, sphincterotome, and/or needle knife. This invention further provides an apparatus for, and a methodology of, accurate control of the depth of the needle knife and the resulting incision and an apparatus which can allow accurate control of the depth of the needle knife while allowing the user to accurately place the needle knife within the patient.

The invention discloses an endoscopic catheter which has a distally located tissue cutting device in a first lumen, and includes a second lumen which has 1) a reciprocating cable inside and 2) includes a fixed member which is used to impart rotary motion to the cable inside of it where the reciprocation of the cable causes a rotation of at least the distal portion of the catheter to orient the cutting device. The cable may have spiral threads on its outer circumference and the fixed member may have spiral threads on its inner circumference which mate with the threads on the cable. The cutting device may be a sphincterotome, a papillotome or a needle knife with a curved distal portion and the cutting device may operate in response to energy from an rf heating source.

In another embodiment a sliding member may be included which is attached to the distal end of the cable and is located distal from the fixed member. The cross section of the lumen containing the sliding member as well as the cross section of the sliding member may be non-round or even square.

In another embodiment of the invention, an endoscopic catheter has a cable actuated needle knife within a lumen where the needle knife is deployable from a distal end of the catheter. In this embodiment the invention substantially prevents movement of the needle knife after deployment and includes a distally positioned fixed stabilizing element in the lumen which internally engages the needle knife cable to prevent such motion. The cable attached to the needle knife may have spiral threads on its outer circumference and the fixed stabilizing element may have spiral threads on its inner circumference which mate with the threads on the cable. The needle knife may have a curved distal portion and the cutting device may operate in response to energy from an rf heating source. A pivot element may be included, preferably proximal to the stabilizing element, to prevent torsion build up within the cable.

In another embodiment, the invention includes an endoscopic catheter having a cable actuated needle knife within a first lumen deployable from a distal end of the catheter and the cutting device may be substantially prevented from movement after deployment. In this embodiment a second lumen containing a reciprocating cable and a fixed member imparts rotary motion to the cable when reciprocated. Reciprocation of the cable causes rotation of at least a distal portion of the catheter to orient the cutting device and a distally positioned fixed stabilizing element in the first lumen internally engages the needle knife cable to substantially prevent movement. The cable may have spiral threads on its outer circumference and the fixed member may have spiral threads on its inner circumference which mate with the threads on the cable. The cutting device may be a needle knife with a curved distal portion and the cutting device may operate in response to energy from an rf heating source. A pivot element and/or a sliding member may be included.

BRIEF DESCRIPTION OF THE DRAWINGS

The various objects, advantages and novel features of this invention will be more fully apparent from a reading of the following detailed description in conjunction with the accompanying drawings in which like reference numerals refer to like parts, and in which.

DESCRIPTION OF ILLUSTRATED EMBODIMENTS

Figure 1:
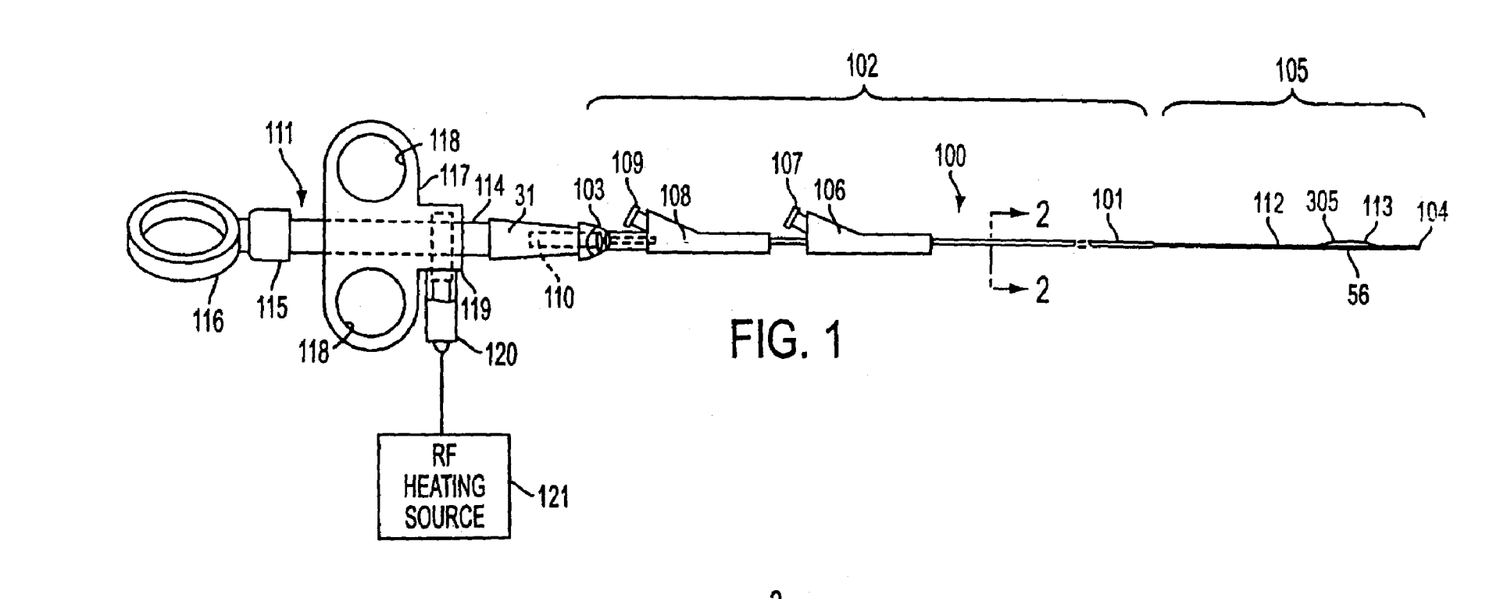
FIG. 1 is a plan view of one embodiment of apparatus constructed in accordance with this invention.

FIG. 1 depicts catheter apparatus 100 that has the capability of injecting a contrast agent into the biliary tree, accurately positioning a cutting wire, of performing a sphincterotomy and of dislodging a gallstone into the duodenum. Apparatus 100 includes a catheter 101 which, for purposes of definition, includes proximal portion 102 extending from proximal end 103 and distal end 104 with distal portion 105 extending a short distance from distal end 104. In a typical application, the catheter will have a working length of 200 cm and distal portion 105 will have a length of 6 cm to 9 cm. Normally distal portion 105 will have a diameter that is smaller than the diameter of proximal portion 102 to increase the flexibility of distal portion 105. The reduction in diameter also makes distal end 104 less traumatic and allows distal portion 105 to reach smaller passages while allowing the larger proximal portion 102 to provide necessary hoop strength and rigidity, particularly where proximal portion 102 is coextensive with the working channel of a duodenoscope. For example, the proximal and distal portions might have diameters corresponding to 7 Fr and 5.5 Fr catheter sizes (i.e., 0.09" and 0.07" respectively).

Figure 2:
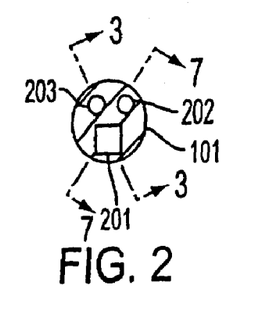
FIG. 2 is a cross-section taken along lines 2—2 in FIG. 1.

As shown particularly in FIG. 2, catheter 101 has three lumens. First lumen 201 has a diameter that is greater than either second lumen 202 or third lumen 203. In one particular embodiment first lumen 201 is square shaped with each side approximately 0.040" in proximal portion 102 that reduces to about 0.037" in distal portion 105 to receive a standard 0.035" guidewire. In addition first lumen 201 may be, and as shown in FIG. 2, is offset from the center of the catheter 101.

The cross section of both second lumen 202 and third lumen 203 are each smaller than the cross section of first lumen 201 and are radially offset from the centerline of catheter 101, from each other and from first lumen 201. In one particular embodiment the cross section of third lumen 203 has a diameter of 0.028" in proximal portion 102 that reduces to about 0.020" in distal portion 105 and second lumen 202 has an internal diameter of 0.028" in proximal portion 102 that reduces to about 0.020" in distal portion 105. As described later, this third lumen 203 carries a cutting wire for performing a sphincterotomy and for allowing the infusion of a contrast agent at reasonable rates. The cutting wire can also be positioned, as described later, as desired. While the description contained herein describes the first lumen 201 having a square cross section shape, it would be apparent to one of ordinary skill in the art that the invention may be practiced in any of the lumens by changing the cross section of the lumen to a shape other than a circle. The angular spacing between second lumen 202 and third lumen 203 is about 45 degrees and the angular spacing between first lumen 201 and each of lumens 202 and 203 each is about 157.5 degrees. In this configuration and with these dimensions proximal portion 102 readily passes through the working channel of any duodenoscope. These angular relationships have been used in the past to position the device. While the invention may be used with these angular relationships, the invention itself allows the device to be positioned which reduces the necessity of strict adherence to the previously used angular relationships.

Referring again to FIGS. 1 and 2, each of lumens 201, 202 and 203 includes an entry port in proximal portion 102 and an exit port in distal portion 105. Generally, and as described in more detail later, first lumen 201 has an exit port through distal end 104 while the exit ports for lumens 202 and 203 can be sited at different locations in distal portion 105 depending upon a particular application.

In FIG. 1, the entry ports in proximal portion 102 adjacent proximal end 103 include an entry port 106 that provides access to first lumen 201 and includes an optional Leur lock fitting 107. Proximally positioned entry port 108 provides access to second lumen 202 and includes optional Leur lock fitting 109. Proximal entry port 110 for third lumen 203 is located coextensively with a portion of handle 111 attached to proximal end 103. One of ordinary skill in the art would understand that this specific configuration is given as an example and not meant to limit the invention. Various other configurations would be apparent to one of ordinary skill in the art to practice the invention described herein.

Referring to the distal portion 105, catheter 101 in this particular embodiment carries expansible balloon 112 proximally of the excursion of cutting wire 113 externally of catheter 101. As described in U.S. patent application Ser. No. 09/154,834 in the name of Rowland, et al., and owned by the owner of the present application and already incorporated herein by reference in its entirety, second lumen 202 emerges at a distal exit port through the side of catheter 101 with the interior of expansible balloon 112. An extension of second lumen 202 beyond the distal port is sealed by known methods of manufacture. Consequently, fluid forced through entrance port 108, as by a syringe (not shown) attached to Leur lock fitting 109, expands balloon 112 into an occluding orientation with an inflated diameter in the range up to 20 mm.

First lumen 201 extends through catheter 101 and terminates with an exit port in distal end 104. Thus first lumen 201 is adapted for receiving a guidewire through the entry port 106 that will extend through catheter 101 and exit distal end 104 and allow the catheter to slide over that guidewire.

Figure 3:
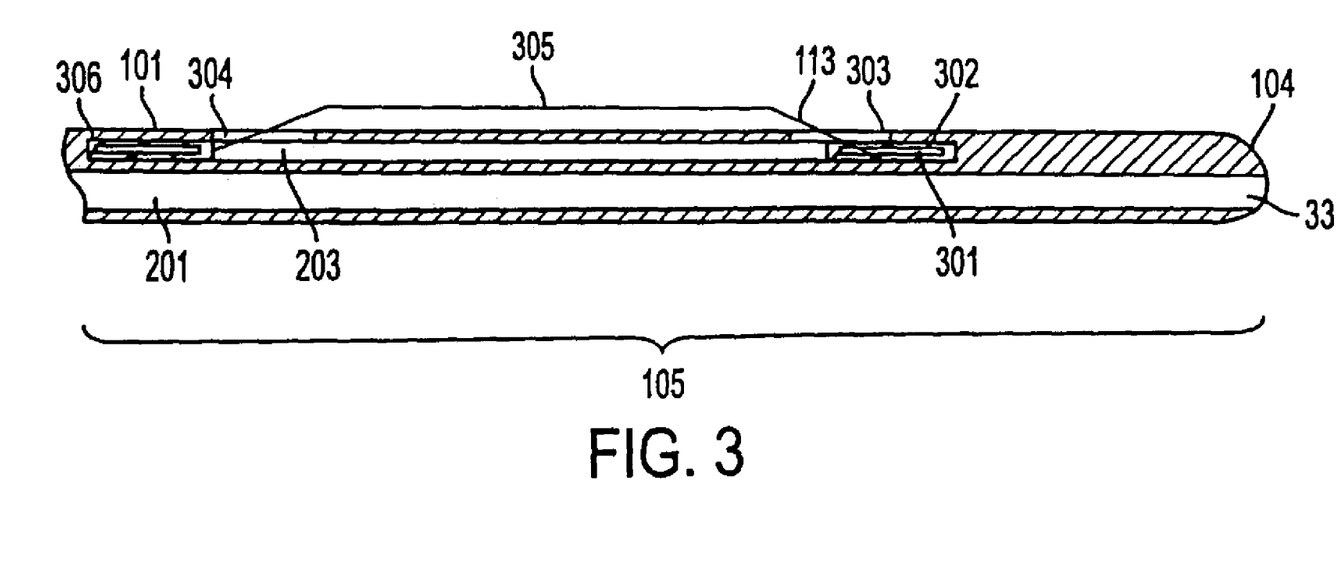
FIG. 3 is a cross-section taken along lines 3—3 in FIG. 2.

Referring to FIG. 3, distal end 301 of cutting wire 113 attaches to a clamp 302 formed at the distal end of third lumen 203. Spaced skived ports 303 and 304 allow active portion 305 of the cutting wire 113 to emerge from catheter 101 through skived aperture 303, parallel the catheter 101 exteriorly thereof and return into third lumen 203 through port 304 and reinforcing sleeve 306. Cutting wire 113 then extends through third lumen 203 to handle 111 shown in FIG. 1 where it emerges as proximal end portion 114.

Handle 111, as shown in FIG. 1, includes central member 115 terminating with thumb ring 116. The central member 115 extends through and slides with respect to body section 117 having opposed finger rings 118. The central member 115 also attaches to catheter 101, and is therefore an extension of catheter 101. Member 117 additionally includes internal connector 119 for clamping proximal end 114 of cutting wire 113. Thus, when body 117 is at its distal position as shown in FIG. 1, distal portion 105 of catheter 101 is in essentially straight line as shown in FIG. 1 with active portion 305 of cutting wire 113 being closely adjacent catheter 101. Retracting body portion 117, causes cutting wire 113 to bend distal end 104 upwardly as shown in FIG. 3 to a position that is essentially at right angles to the main axis of the catheter, as will be shown later.

Connector block 119 and cutting wire 113 are generally conductive members that attach through RF connector 120 to RF heating source 121. The use of such RF heating sources 121 for energizing cutting wire 113 thereby to cut the sphincter muscle is well known in the art and represents one possible sphincterotomy procedure that can be adapted for the apparatus of this invention and is not described further.

Figure 4:
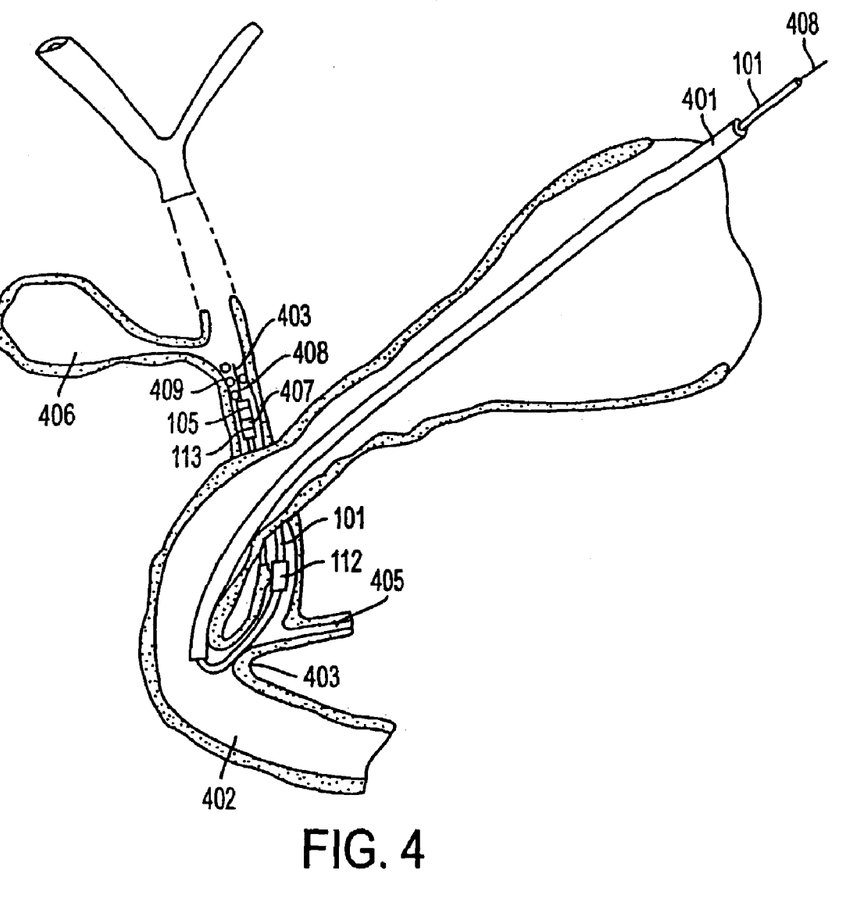
FIG. 4 depicts the apparatus of FIG. 1 positioned through a duodenoscope for injecting contrast agent into the biliary tree.

With this description of the apparatus structure, it will now be possible to understand its use in a particular application. FIG. 4 discloses, in a partially broken and schematic view, the positioning of duodenoscope 401 in duodenum 402 adjacent sphincter of Oddi 403. Catheter 101 such as constructed in FIG. 1 passes through sphincter of Oddi 403 into the common bile duct 404, bypassing pancreatic duct 405. Distal end 104 does not extend to gallbladder 406.

Fluoroscopy allows the appropriate positioning by utilizing a series of radio-opaque markers 406 at distal portion 105 that may include clamp 302 and reinforcing sleeve 306 in FIG. 3. Catheter 101 can be positioned with or without the presence of guidewire 408 in first lumen 201 shown in FIGS. 2, and 3. For purposes of injecting the contrast agent, any guidewire 408 can be withdrawn to allow the contrast agent to be injected through first lumen 201 for purposes of fluoroscopic examination to confirm the presence of one or more gallstones 409. It is also possible during the operation to expand balloon 112 to occlude common bile duct 404 and block any migration of contrast agent into duodenum 402 or pancreatic duct 405.

Figure 5:
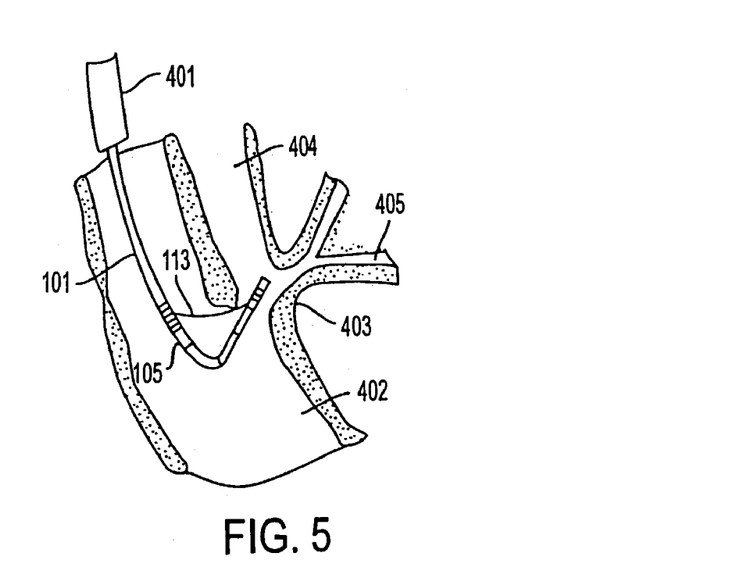
FIG. 5 is an enlarged view that depicts the orientation of the apparatus in FIG. 1 for performing a sphincterotomy.

FIG. 5 is an enlarged view showing duodenum 402, sphincter of Oddi 403, portions of pancreatic duct 405 and common bile duct 404. In FIG. 5 catheter 101 has been positioned relative to the duodenoscope 401 through the opening of sphincter of Oddi 403. The handle 111 in FIG. 1 has been drawn proximally to deflect distal portion 105 into essentially a right angle configuration such that cutting wire 113 abuts a portion of sphincter of Oddi 403. The application of RF heating to cutting wire 113 then will cut sphincter of Oddi 403 and enlarge the opening therethrough. As will be apparent, the sphincterotomy is performed with direct visualization of the sphincter of Oddi through the duodenoscope.

Moreover, as has been observed by others, catheters having guidewire and cutting wire lumens tend to assume a particular angular orientation when distal portion 105 emerges from the duodenoscope. This orientation is essentially independent of the angular position of the catheter when it is inserted into the duodenoscope. The offset nature of lumen 203 as shown in FIG. 2, improves the location of cutting wire 113 as distal portion 105 passes through sphincter of Oddi 403. Specifically the angularly offset brings cutting wire 113 into better alignment with common bile duct 404 and displaces the cutting wire from pancreatic duct 405.

Figure 6:
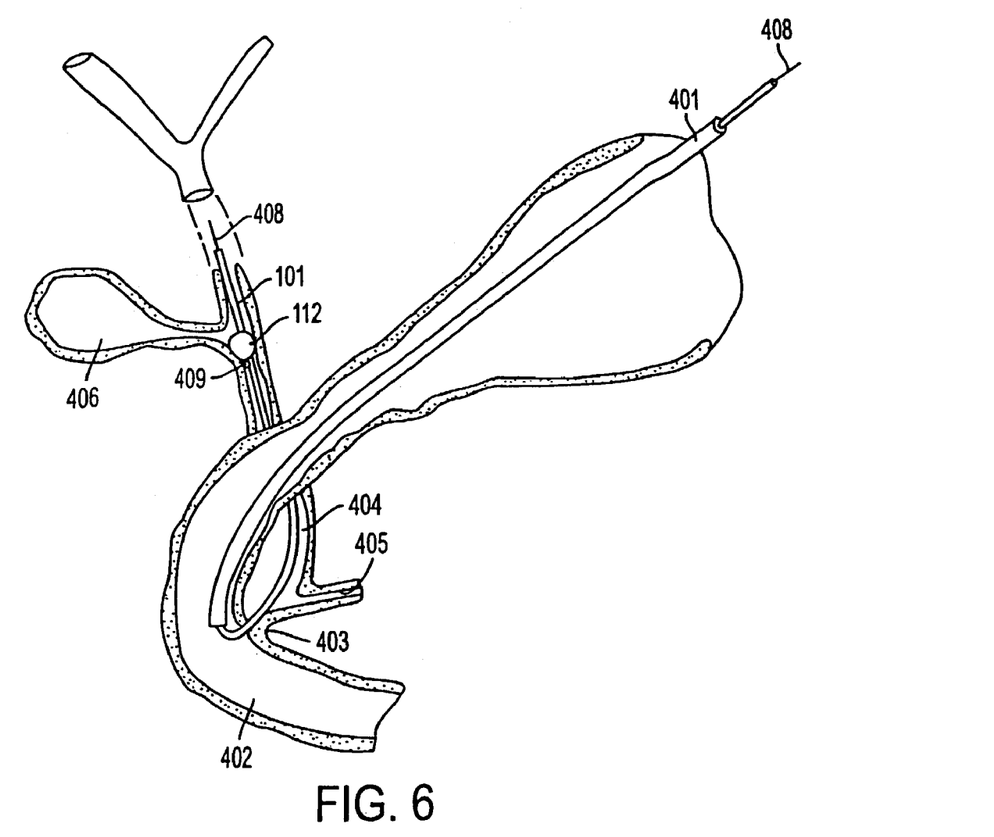
FIG. 6 depicts the apparatus of FIG. 1 positioned through a duodenoscope for dislodging material within the common bile duct.

FIG. 6 depicts the catheter after the sphincterotomy and after catheter 101 is advanced over guidewire 408, if used. FIG. 6 also discloses catheter 101 after balloon 112 has been moved beyond gallstone 409 in bile duct 404. Balloon 112 is expanded so that upon withdrawal of catheter 101 balloon 112 will dislodge gallstones 409 and sweep them through sphincter of Oddi 403 into duodenum 402.

As will now be apparent from the description of the particular catheter apparatus 100 shown in FIG. 1 and its use as discussed with respect to FIGS. 4, 5, and 6, the single catheter apparatus is capable of providing diagnostic contrast agent injection, of performing a sphincterotomy and of dislodging gallstones in the common bile duct or other portions of the biliary tree without having to exchange a catheter. Moreover, positioning and sizing of the lumens enables these functions to be performed with a catheter apparatus that is readily adapted for use in the working channels of standard duodenoscopes. Consequently the gallstones can be removed from the biliary tree without bile duct incisions and accompanying surgical procedures, as duodenoscope can be introduced through the alimentary tract. Consequently the entire procedure is adapted for being performed more rapidly than prior art procedures and with fewer components. The net effect is to reduce patient trauma and the overall time and cost of conducting the procedure.

Figure 7:
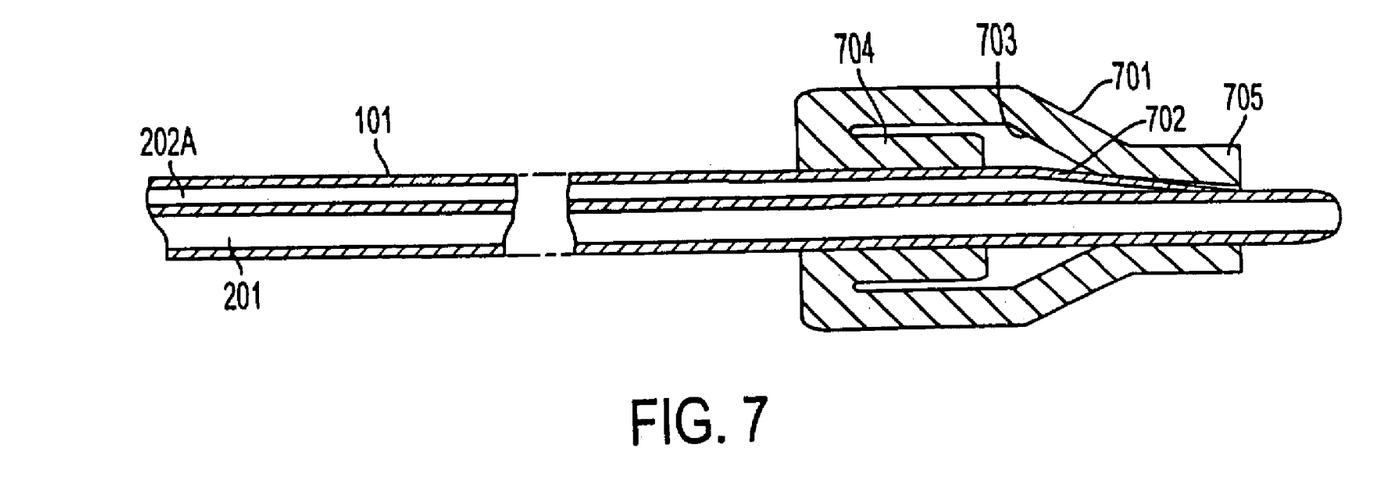
FIG. 7 is a cross-section of an alternative embodiment of the apparatus as viewed generally along lines 7—7 in FIG. 2.

In FIG. 1 balloon 112 is located proximally of cutting wire 113. FIG. 7 discloses an alternative embodiment in which balloon 701 is located distally of cutting wire 113. More specifically, the distal end of lumen 202A, corresponding to second lumen 202 in FIG. 3 is sealed. Side facing exit port 702 skived or otherwise formed in catheter 101 opens into chamber 703 formed by balloon 701. First sealing portion 704 and a sealing portion 705 of balloon 701 connect proximally and distally of aperture 702 respectively and seal chamber 703.

Introduction of a balloon inflation fluid through lumen 202A expands balloon 701 into an occluding orientation corresponding to the orientation of balloon 701. Retraction of catheter 101 with distal balloon 701 inflated enables withdrawal of a gallstone from the bile duct. This particular embodiment is particularly adapted when it is determined that a gallstone is located high in the biliary tree to minimize the incursion of distal portion 105 through the biliary tree beyond the gallstone or in any application in which the internist desires to minimize the length of distal portion 105 that extends beyond the occluding balloon.

Figure 8:
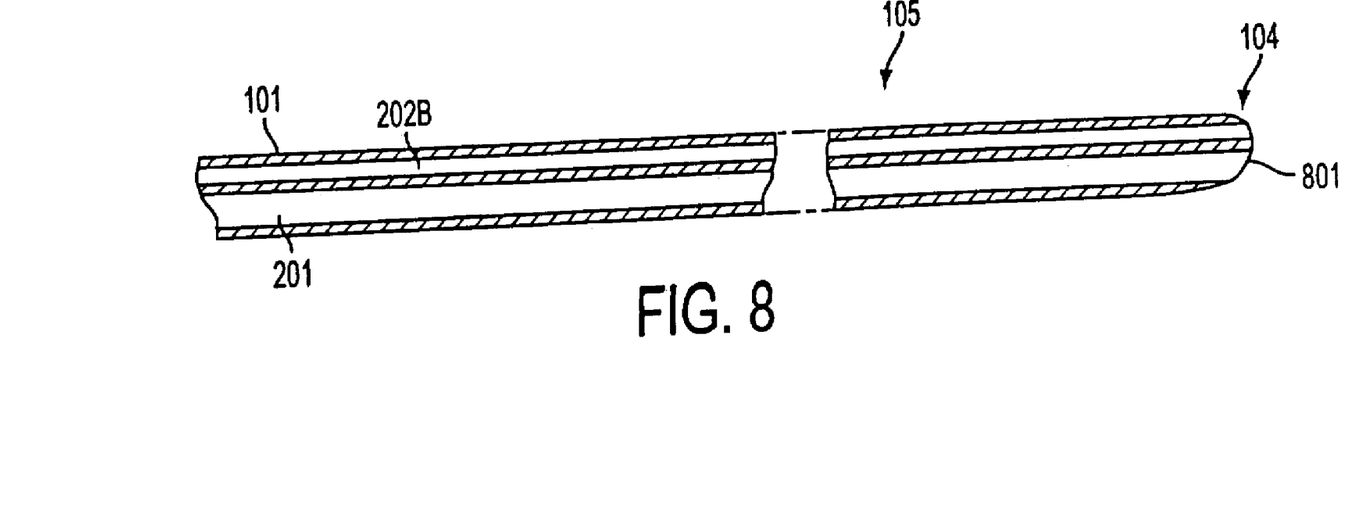
FIG. 8 is a cross-section of still another embodiment of the apparatus taken along lines 7—7 in FIG. 2.

FIG. 8 discloses another embodiment for enlarging the sphincter of Oddi and performing another procedure, such as injecting a contrast agent into the biliary tree, as might be used in the diagnosis and treatment of a stricture in the biliary tree. In this particular embodiment exit port 801 from second lumen 202B is located in distal end 104 of distal portion 105. First lumen 201 then can be used for a guidewire and lumen 202B, for injecting the contrast agent directly into the biliary tree while the guidewire remains in place. The apparatus would then be positioned to perform a sphincterotomy without having to exchange a catheter should the procedure be warranted.

As still another alternative, the internist could utilize a conventional catheter for purposes of injecting the contrast agent to determine the need for gallstone removal. If treatment were indicated, the internist could then utilize apparatus as shown in FIG. 1 with a single exchange over the guidewire that would pass through lumen 201 as previously described.

As can be seen from the above description one of the steps in the treatment of obstructive disease is normally the practice of tissue incision which is achieved by advancing a cutting wire endoscopically to the target site. As explained above, once the catheter tip is in position, the catheter tip is bowed (FIG. 5) to expose cutting wire 113 to tissue. Diathermic current is passed through cutting wire 113 from RF Heating Source 121 (FIG. 1) which allows the endoscopist to incise and cauterize the tissue at the target site. Safe and effective results are only obtained through precision positioning of cutting wire 113.

Figure 9:
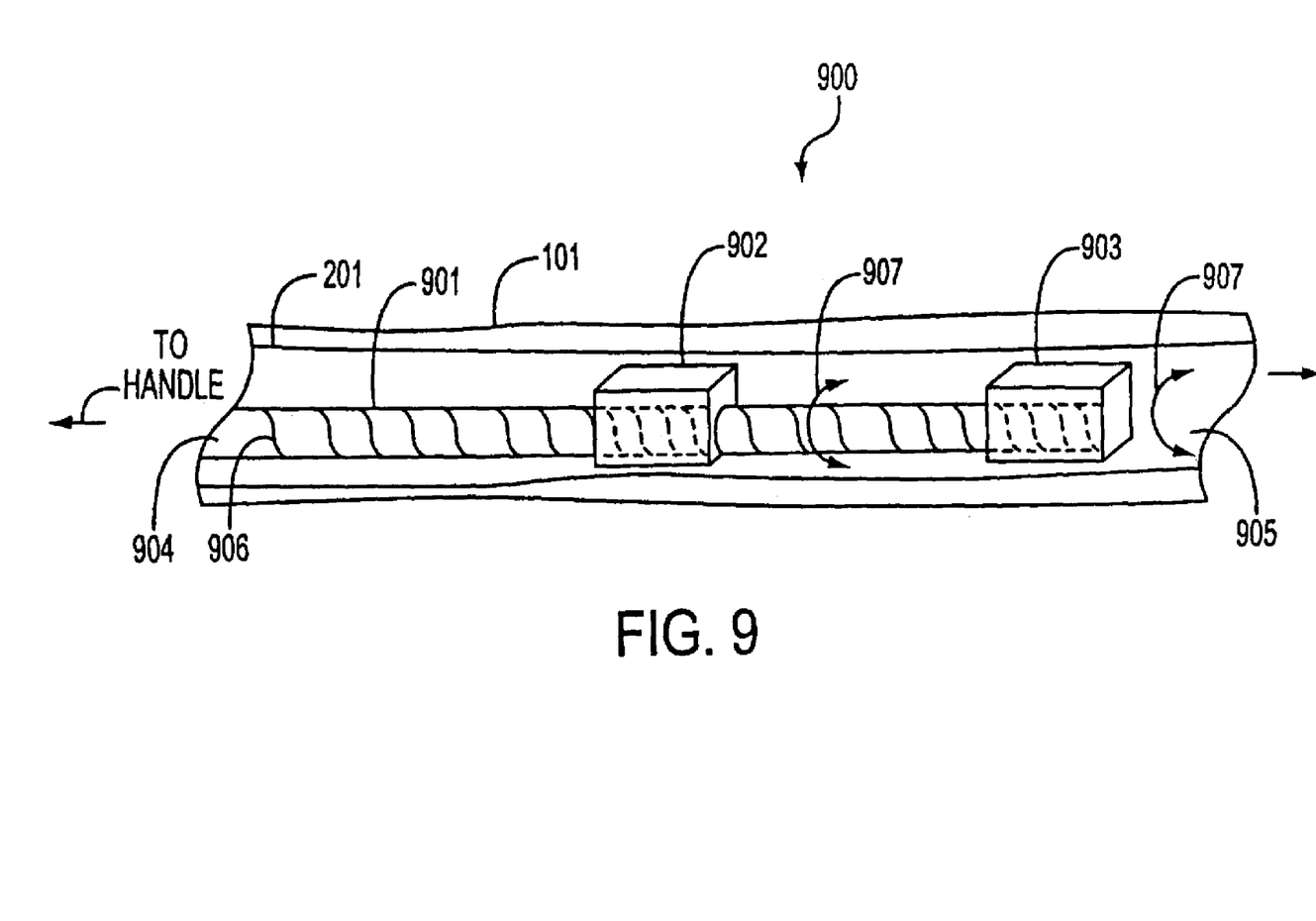
FIG. 9 is a partial cross-section of the invention highlighting the positioning device.

FIG. 9 depicts a section of a positioning device 900 residing within lumen 201 of a multi-lumen catheter 101. As shown in FIG. 2 lumen 201 has an internal shape, in this case a square, which allows the positioning device 900 to transfer torque to distal end 104. The internal shape of lumen 201 in FIG. 2 is depicted to be a square, but one of ordinary skill in the art would understand that any internal shape which allows the torque transfer may be used and is within the disclosed invention. Referring back to FIG. 9, positioning device 900 consists of cable assembly 901, which is substantially encircled by torque transmission element 902 and cog 903. Proximate end 904 of positioning device is attached to handle 111 (not shown) while distal end 905 of positioning device 900 is located in the distal portion 105 (not shown). While FIG. 9 illustrates a torque transmission element 902 which completely encircles cable assembly 901, it would be apparent to one of ordinary skill in the art that torque transmission element 902 need not entirely encircle cable assembly 901 and any configuration between torque transmission element 902 and cable assembly 901 which allows the translation of reciprocal movement to rotational motion is within the scope of the invention. The cog 903 can also be referred to as a sliding member.

Cable assembly 901 is connected at its proximal end (not shown) to the distal end of handle 111, traverses through lumen 203 and torque transmission element 902 with the distal end of cable assembly 901 fixed to cog 903. Reciprocal motion of the handle 111 attached to the cable assembly 901 introduces reciprocal motion in the proximal portion of the cable assembly 901 between the handle 111 and torque transmission element 902. The outer circumference 906 of the cable assembly 901 includes a helical or advancing spiral thread.

The torque transmission element 902 is located and fixed within lumen 201 a short distance from distal end 104 (FIG. 1) and proximal to cog 903. The internal portion of torque transmission element 902, or the portion which comes into contact with the cable assembly 901, contains a helical or advancing spiral thread which interacts and mates with the helical or advancing spiral thread of cable assembly 901. The external portion of torque transmission element 902, or the portion which comes into contact with lumen 201, is shaped to interact with and mate with the interior surface of lumen 201 and is fixed to inner lumen 201. The purpose of torque transmission element 902 is to change the reciprocal cable movement received from the reciprocal movement of the attached handle 111 to rotational cable movement in direction 907. The torque transmission element 902 may be molded as part of or attached to lumen 201.

The cog 903 is located between torque transmission element 902 and distal end 104 and at a distance from each so as to aid in creating effective rotation of the catheter distal end 104. This rotation, in the direction of 907, is the result of the torque transmission element 902 translation of the reciprocal movement received from handle 111 into rotational cable movement. As torque transmission element 902 receives reciprocal movement from cable assembly 901, torque transmission element 902 cannot moved because it is fixed to lumen 201 and the internal helical or advancing spiral inside of torque transmission element 902 imparts a rotational affect on cable assembly 901 in a similar manner to the spin a bullet receives from the rifling inside of a rifle's barrel. Cog 903 is not fixed to lumen 201 and is capable of reciprocal movement within lumen 201 as the cable assembly 901 advances and retracts. The purpose of cog 903 is to transfer the torque received from cable attached to torque transmission element 902 to the distal segment of the catheter and this is achieved when cog 903 is fixed to cable assembly 901. While the invention is shown with cog 903, one of ordinary skill in the art would understand that the cog 903 is not absolutely necessary to the invention, but instead aids in the transmission of the torque created by torque transmission element 902. Cog 903, while included in the preferred embodiment, may be eliminated and the distal tip 104 would still be capable of being positioned. The resistance between the torque transmission element 902 and the cable assembly 901 may be varied to adjust the proportion of the reciprocal movement which is translated into rotational motion. Cog 903 may also be shaped to increase the efficiency of the transfer of rotational movement from the distal end of the cable to the distal segment of the catheter. For example, where the cross-section of lumen 201 is in the shape of a square the cross section of cog 903 would also be a square.

In operation distal end 104 of the cutting device is advanced through the lumen 203 of the endoscope to the target area. Cutting wire 113 is retracted to bow the tip exposing the cutting wire (FIG. 5). The distal end of device 900 is advanced through lumen 201 until torque transmission element 902 is in, or near the distal portion 105. The handle 111, which is connected to cable 901, is reciprocated, causing the proximal end 904 of cable assembly 901 to be reciprocated. When the proximal end of cable assembly 901 is reciprocated, torque transmission element 902 translates this movement into rotation which is transferred from cog 903 to the catheter distal end 104. As catheter distal end 104 is rotated so is cutting wire 113 which resides in lumen 203. After the incision is made in the target area, cutting wire 113 is advanced relieving the bow. The catheter assembly can then be removed from the body. Overall, the effect of the positioning system 900 is to translate the reciprocal movement in the handle 111 into rotational movement at the distal end 104 of the catheter.

Figure 10:
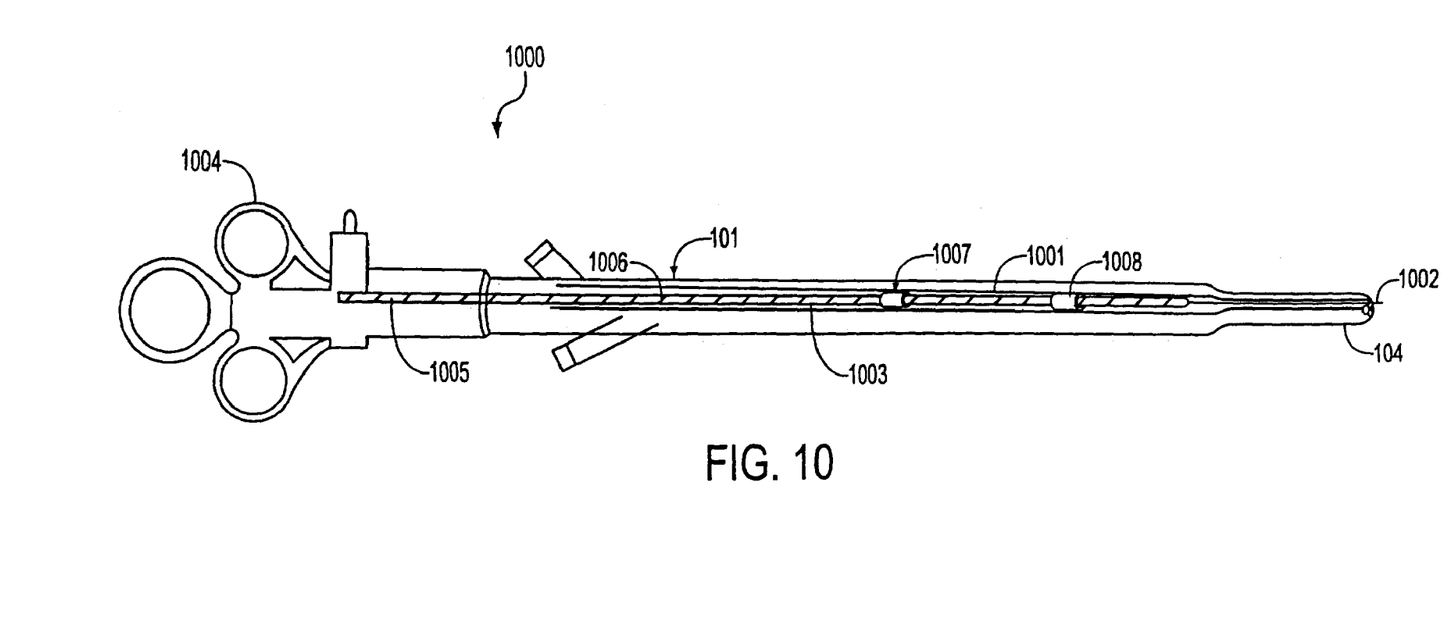
FIG. 10 is a cutaway view of an alternative embodiment of the present invention used to support the extension of the needle knife.

FIG. 10 depicts a multi-lumen catheter 1000 which includes an alternate embodiment of the present invention for the precise positioning of a needle knife. Within catheter 101 of multi-lumen catheter 1000 is lumen 1001 which is used for needle knife 1002. Within lumen 1001 resides needle knife wire 1003. Needle knife wire 1003 is attached at the proximal end to a sliding mechanism of handle 1004 and on the distal end to needle knife 1002. Needle knife 1002 is capable of extending beyond distal end 104 of catheter 101. Circumference 1005 of needle knife wire 1003 includes helical or advancing spiral 1006. FIG. 10 shows helical or advancing spiral 1006 along the entire length of needle knife wire 1003, but helical or advancing spiral 1006 portion of needle knife wire 1003 need not be included along the entire length and may be limited to inclusion over a short distance of needle knife wire 1003 close to the distal end 104. Helical or advancing spiral 1006 is required where pivot element 1007 and stabilizing element 1008 attach and along needle knife wire 1003 where pivot element 1007 and stabilizing element 1008 may travel. In one embodiment the helical or advancing spiral 1006 may be located between 6 and 10 cm from the distal end.

Pivot element 1007 and stabilizing element 1008 are attached to needle knife wire 1003. Pivot element 1007 is located proximal to stabilizing element 1008 and is used to prevent torsion build up. While the preferred embodiment includes pivot element 1007, the invention can be practiced without the inclusion of pivot element 1007. Stabilizing element 1008 is located a short distance from distal end 104 and may be molded as part of the lumen or attached to the lumen. In one embodiment the stabilizing element 1008 was located 6 to 10 cm from the distal tip. The purpose of the stabilizing element is to prevent needle knife 1002 from being pushed back into lumen 1001 when pressure is applied to the needle knife 1002, for example when an incision is made. The stabilizing element 1008 is part of or fixed to the lumen wall and uses this attachment to prevent the needle knife 1002 from being pushed back into the lumen. Stabilizing element 1008 may have a helical or advancing spiral 1109 (FIG. 11B) along its inner circumference which mates with the helical or advancing spiral 1006 of needle knife wire 1003.

When the sliding mechanism of handle 1004 which is attached to needle knife wire 1003 reciprocates, needle knife wire 1003 also reciprocates. As needle knife wire 1003 reciprocates, threaded needle knife wire 1003 rotates through stabilizing element 1008 and needle knife 1002 advances out of or retracts into lumen 1001. The sliding mechanism of handle 1004 can be locked when needle knife 1002 is deployed to its desired length. As pressure is applied to needle knife 1002 during incision any forward or backward movement of needle knife 1002 is negated by stabilizing element 1008 which acts, to resist movement of the needle knife back into the lumen 1001. This resistance is created by the interaction of the matched helical windings of the stabilizing element 1008 and the needle knife wire 1003. Stabilizing element 1008 allows needle knife 1002 to be locked regardless of the overall catheter length.

In operation distal end 104 of device 100 is advanced through the endoscope to the target area. Needle knife wire 1003 is advanced via the sliding mechanism of handle 1004 to expose needle knife 1002 to the desired length. The sliding mechanism of handle 1004 is then locked into position. As pressure is applied to needle knife 1002 during the incision, stabilizing element 1008 ensures the integrity of the depth of cut of needle knife 1002. Once the incision is made in the target area, needle knife 1002 is retracted and the catheter assembly is removed from the body.

Figure 11A:
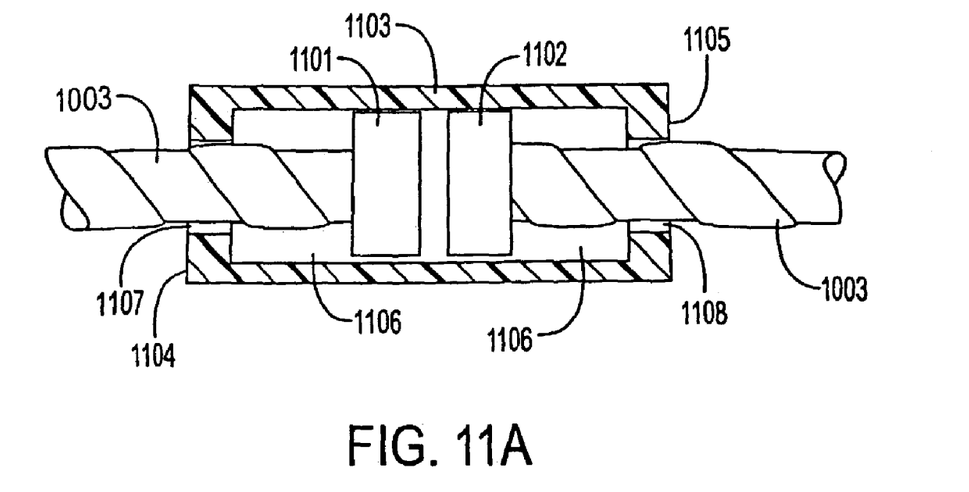
FIGS. 11A and 11B are enlarged views of the a pivot element and a stabilizing element from FIG. 10.
Figure 11B:
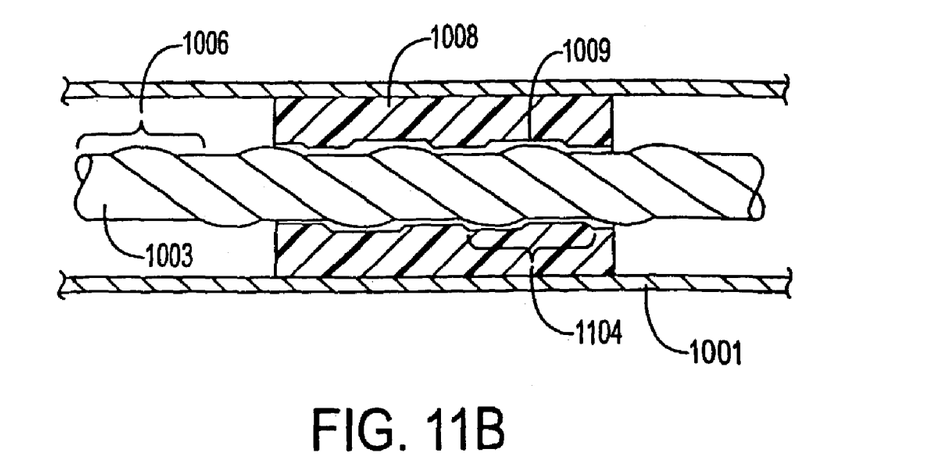

FIGS. 11A and 11B show a blown up diagram of the pivot element 1007 and the stabilization elements 1008 respectively. The pivot element shown in FIG. 11A, consists of three parts, a proximal element 1101, a distal element 1102 and an enclosure element 1103. When the needle knife wire 1003 is pushed towards the distal end 104, proximate element 1101 makes contact with distal element 1102 and ensures the entire needle knife wire progresses within the lumen toward the distal end 104. When the needle knife wire 1003 is retracted, proximal element 1101 contacts the proximal portion 1104 of the enclosure element 1103 and the distal portion 1105 of the enclosure element 1103 contacts the distal element 1102 and ensures the entire needle knife wire is retracted. Within the pivot element 1007 is a space 1106 between the proximal element 1101 and the distal element 1102 and the sides of the enclosure element 1103. There is also a space 1107 between the needle knife wire 1003 and the entrance 1107 and exit 1108 of the enclosure element 1103. The stabilizing element 1008 is shown in FIG. 11B which highlights the mating 1104 between the helical windings on the needle knife wire 1003 and the stabilizing element 1008.

Figure 12:
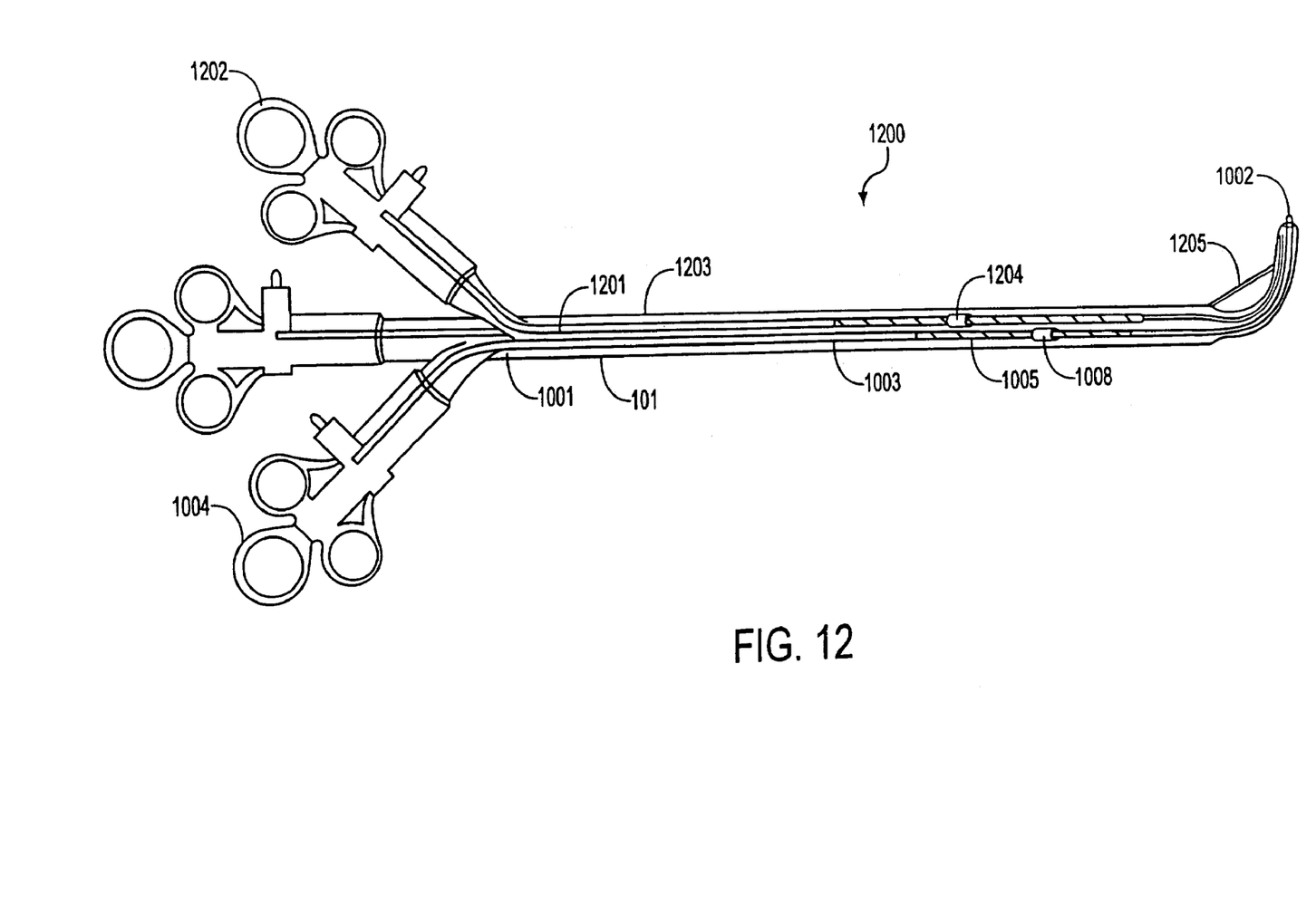
FIG. 12 is a plan view of an alternate embodiment of the present invention which combines a positioning device and a support for the needle knife.

FIG. 12 is a perspective view of a device which incorporates both a stable needle knife to maintain the blade depth and which allows the user to position the blade in a desired direction. Within catheter 101 of multi-lumen catheter 1200 is lumen 1001 which is used for needle knife 1002. Within lumen 1001 resides needle knife wire 1003. Needle knife wire 1003 is attached at the proximal end to a sliding mechanism of handle 1004 and on the distal end to needle knife 1002. Needle knife 1002 is capable of extending beyond distal end 104 of catheter 101. The circumference 1005 of needle knife wire 1003 includes helical or advancing spiral 1006. In one embodiment the helical or advancing spiral 1006, 6 cm of the needle knife wire includes the helical or advancing spiral feature which is located at a distance of 12 cm from the distal tip. Needle knife (stabilizing) threaded element 1008 is also included in the device 1200 to prevent the blade 1002 from being pushed back into the lumen when pressure is applied to the needle knife blade 1002. The mechanism of FIG. 12 which prevents the blade of the needle knife 1002 from being pushed back into the lumen has been described with respect to FIG. 10. The needle knife (stabilizing) threaded element may be molded as part of or attached to the lumen. A pivot element 1007 (FIG. 10) may be attached to the needle knife wire 1003 if desired.

FIG. 12 also includes a mechanism for steering the position of the cutting wire 113. Steering wire 1201 is connected at its proximal end to the distal end of handle 1202, traverses through lumen 1203 and steering wire threaded element 1204. The internal surface of steering wire threaded element 1204 matches and mates with the external circumference of steering wire 1201. As the steering wire 1201 is reciprocated via a sliding mechanism on handle 1202, the threaded steering wire 1201 rotates through the steering wire threaded element 1204. This rotation causes the distal section of the catheter to rotate. The sliding mechanism can be locked when the desired position is achieved. In one embodiment the distal end of the steering wire 1201 was threaded for 10 cm at a distance of 8 cm from the distal tip. The major advantage of device 1200 is the ability to rotate the distal tip either clockwise or counterclockwise as the sliding mechanism is reciprocated and to ensure the blade of the needle knife does not retract into the lumen when used. The steering wire threaded element may be molded as part of or attached to the lumen. A cog 903 (FIG. 9) may also be included for a more effective transfer of rotational position to the distal end 104.

FIG. 12 also shows a bowing wire 1205 included in device 1200. The inclusion of the bowing wire 1205 allows the distal tip of the catheter to be turned up to 90 degrees from the longitudinal axis of the catheter body 101.

In operation the distal tip of the device is advanced through lumen 1001 of the endoscope to the target area. Once the distal tip reaches the target area, the tip of the catheter is bowed to the desired angle. The steering device is then advanced through lumen 1203 until the steering element is in, or near, the distal portion 105. The tip of the catheter is than rotated to the desired position and locked when the desired position is obtained. The needle knife is than advanced to expose the needle knife to the desired length. Once the exposed length is attained, the handle is locked to ensure the needle knife blade is not pushed back into the lumen when pressure is applied to it. The incision is then made in the target area and the needle knife is retracted, the bow is released and the catheter assembly is removed from the body.

Therefore, it will now be apparent that apparatus constructed in accordance with this invention attains the several objects and the advantages of this invention. More particularly, catheter apparatus constructed in accordance with this invention allows the injection of a contrast agent, the performance of a sphincterotomy and dislodging gallstones from the common bile duct through the enlarged sphincter of Oddi into the duodenum all without requiring any catheter exchanges. Moreover, this apparatus allows such a procedure to occur through a duodenoscope to minimize patient trauma. The use of a single catheter with an elimination of catheter exchanges further reduces the time and costs associated with the use of multiple, single-function catheter devices.

As will be apparent from the foregoing description, many alterations can be made to the specifically disclosed embodiments. Different balloon structures can be used and located at alternative positions. Different cutting wire embodiments and orientations can be used. Thus, although this invention has been disclosed in terms of certain embodiments, it will be apparent that many modifications can be made to the disclosed apparatus without departing from the invention. In particular, it is considered that all of the foregoing embodiments may be used in conjunction with a handle fixed to the cutting wire but rotatable relative to the catheter. Therefore, it is the intent of the appended claims to cover all such variations and modifications as come within the true spirit and scope of this invention.

The invention claimed is:

1. A multi-lumen, multi-functional endoscopic catheter comprising:

a first lumen disposed in said catheter;

at least one positionable cutting device disposed in said first lumen to be positioned along said first lumen and also out of a distal end of said first lumen a reciprocating cable disposed in said first lumen to position said cutting device;

at least one transmission element disposed in said first lumen at a distal portion of said catheter, said transmission element being disposed about said cable;

said cable having a helical exterior shaped surface portion that is in moveable contact with a helical interior shaped surface portion of said transmission element so that when a proximal portion of said cable is reciprocally moved a combination of rotational and reciprocal movements are made between said cable and said transmission element as said cable helical exterior shaped surface portion is moved with respect to said transmission element helical interior shaped surface portion; and, said transmission element having an exterior shaped surface disposed in contact with an interior shaped surface of said first lumen for transmitting rotary motion to the distal end of said catheter from said transmission element.

2. The catheter of claim 1 further comprising an expansible balloon at the distal end of a second lumen, said second lumen open at the distal end of said catheter to the interior of said balloon and open at the proximal end of said catheter to an entrance port.

3. The catheter of claim 1 further comprising:

a second lumen for receiving a guidewire.

4. The catheter of claim 1 further comprising:

a bendable cutting wire energized by radio-frequency energy.

5. The catheter of claim 1, wherein said catheter is insertable in a duodenoscope.

6. The catheter of claim 1, wherein said transmission element completely encircles said cable.

7. The catheter of claim 1, wherein said transmission element is fixed to the inner surface of said first lumen.

8. The catheter of claim 1, further comprising:

a cog located in said first lumen and having an exterior shaped surface that is the same as the interior shaped surface of said first lumen, said cog capable of reciprocal movement within said first lumen.

9. The catheter of claim 1, wherein resistance between said transmission element and said cable is varied to change the proportion of reciprocating motion transmitted to rotary motion.

10. The catheter of claim 1, further comprising:

a cog located in said first lumen and having an exterior shaped surface that is different from the interior shaped surface of said first lumen said cog capable of reciprocal movement within said first lumen.

* * * * *